United States Patent [19]

Ottlinger et al.

[11] Patent Number: 4,870,200

[45] Date of Patent: Sep. 26, 1989

[54] PROCESS FOR PREPARING DISPROPORTIONATION PRODUCTS OF DICHLOROMETHYLSILANE IN THE PRESENCE OF A CATALYST

[75] Inventors: Ralph Ottlinger, Murnau; Alfred Rengstl, Reischach; Reinhard Jira, Burghausen, all of Fed. Rep. of Germany

[73] Assignee: Wacker-Chemie GmbH, Munich, Fed. Rep. of Germany

[21] Appl. No.: 176,501

[22] Filed: Apr. 1, 1988

[30] Foreign Application Priority Data

Apr. 10, 1987 [DE] Fed. Rep. of Germany ....... 3712098

[51] Int. Cl.$^4$ .............................................. C07F 7/08
[52] U.S. Cl. ................................................... 556/469
[58] Field of Search ........................................ 556/469

[56] References Cited

U.S. PATENT DOCUMENTS

| | | | |
|---|---|---|---|
| 3,384,652 | 5/1968 | Hamilton | 556/469 |
| 3,980,686 | 9/1976 | LeFort et al. | 556/469 |
| 4,605,543 | 8/1986 | LePage et al. | 556/469 X |
| 4,667,048 | 5/1987 | Inoue et al. | 556/469 |
| 4,746,752 | 5/1988 | LePage et al. | 556/469 |

*Primary Examiner*—Paul F. Shaver

[57] ABSTRACT

The present invention provides a process for preparing disproportionation products of dichloromethylsilane in the presence of a catalyst, which comprises contacting dichloromethylsilane with a catalyst consisting of a carrier which is insoluble in the reaction medium and having $NR_3$ groups or $^-X^+NR_4$ groups covalently bonded thereto, in which R represents the same or different alkyl, aryl, or alicyclic groups which may contain heteroatoms as constituents of the ring, or represents a hydrogen radical, and $X^-$ represents a chloride, bromide or iodide.

3 Claims, No Drawings

PROCESS FOR PREPARING DISPROPORTIONATION PRODUCTS OF DICHLOROMETHYLSILANE IN THE PRESENCE OF A CATALYST

The present invention relates to a process for preparing disproportionation products and more particularly to a process for preparing disproportion products from dichloromethylsilane in the presence of a catalyst.

BACKGROUND OF THE INVENTION

The disproportionation of dichloromethylsilane to form chloromethylsilane and/or methylsilane in the presence of a catalyst by exchange of Si-bonded hydrogen and chlorine atoms is well known in the art. In this reaction, the disproportionation of dichloromethylsilane to form methylsilane may proceed via chloromethylsilane as an isolated intermediate.

U.S. Pat. No. 4,405,590 to Simon et al describes the disproportionation of halogenosilanes by contacting a halogenosilane having at least one Si-H function with compounds containing at least one alpha-oxoamino group as disproportionation catalysts, and U.S. Pat. No. 2,834,648 to Bailey et al describes treating chlorosilanes with secondary or tertiary aliphatic amines, their salts and derivatives, and heterocyclic amines as disproportionation catalysts. In these processes, the catalyst is homogeneously distributed in the reaction medium, so that the reaction takes place in a homogeneous phase, thereby making it difficult to separate and recover the catalysts.

It is an object of the present invention to provide a process for preparing disproportionation products of dichloromethylsilane, in which the catalysts can be easily removed and separated and thereby reduce the amount of foreign substances present in the resultant chlorosilanes and silanes. Another object of the present invention is to provide a continuous process for preparing chlorosilanes and silanes while providing a means for recovering the catalyst without any additional expenditure in terms of technology or time.

SUMMARY OF THE INVENTION

The foregoing objects and others which will become apparent from the following description are accomplished in accordance with this invention, generally speaking, by providing a process for preparing disproportionation products of dichloromethylsilane which comprises contacting the dichloromethylsilane with a catalyst consisting of a carrier which is insoluble in the reaction medium and having $NR_3$ groups or $-X^+NR_4$ groups covalently bonded thereto, in which R represents the same or different alkyl, aryl or alicyclic groups which may contain heteroatoms as constituents of the ring or represents a hydrogen radical and $X^-$ represents chloride, bromide or iodide.

DESCRIPTION OF THE INVENTION

In the groups represented by $NR_3$ and $-X^+NR_4$, which are covalently bonded to the carrier, R is preferably an alkyl group having from 1 to 20 carbon atoms per radical, such as methyl, ethyl, n-propyl, isopropyl, n-butyl, sec-butyl, decyl, dodecyl, tetradecyl, hexadecyl and octadecyl radicals. Examples of aryl groups represented by R are phenyl and tolyl radicals. Examples of alicyclic groups represented by R, which are free of heteroatoms as constituents of the ring are $-(CH_2)_5-$ and $-(CH_2)_4-$ radicals, and an example of alicyclic groups represented by R which have a heteroatom as a constituent of the ring is a $-(CH_2)_2-O-(CH_2)_2-$ radical. The methyl radical is a preferred example of an alkyl group represented by R and the chloride ion is a preferred example of the halide ion $X^-$.

Preferred carriers which are insoluble in the reaction medium are substances having hydroxyl groups on their surface. Examples of such substances are acidic clays, such as for example Tonsil, montmorillonite and other aluminosilicates in the $H^+$-form, zeolites, porous glass such as, for example, controlled pore glass or porous ceramics such as controlled pore ceramics, porous silicon dioxide, such as precipitated or pyrogenic silica, porous alumina and porous mullite. Additional examples of preferred carriers which are insoluble in the reaction medium are dried hydrolysis products of functional silanes or polystyrenes, such as, for example, polystyrene which is crosslinked with divinylbenzene.

Porous silicon dioxide or polystyrene crosslinked with divinylbenzene are particularly preferred as carriers.

In compounds having hydroxyl groups on their surface the covalent bond between the $NR_3$ groups or $-X^+NR_4$ groups and the carrier are formed by reacting these hydroxyl groups with the hydrolyzable groups Y of the compounds of the formula

$$Y_{3-x}R^1{}_xSi(CH_2)_nZ,$$

in which Y represents a hydrolyzable group and $R^1$ is an alkyl or aryl group, n is in the range of from 1 to 20, x is 0 or 1 and Z represents the groups $NR_2$ and $-X^+NR_3$, where R is the same as above, in an inert solvent at temperatures in the range of from 0° to 200° C.

Hydrolyzable groups represented by Y are preferably alkoxy radicals, such as methoxy or ethoxy radicals, or halogen atoms such as a chlorine atom, alkyl groups represented by $R^1$ are preferably hydrocarbon groups having from 1 to 12 carbon atoms, such as methyl, ethyl, n-propyl, isopropyl, n-butyl, or isobutyl radicals, and aryl groups represented by $R^1$ are preferably phenyl and tolyl radicals. The methyl radical is the preferred radical represented by $R^1$ and n is preferably 2 or 3, that is an ethylene or propylene radical.

Examples of preferred compounds of the formula

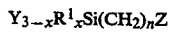
$$Y_{3-x}R^1{}_xSi(CH_2)_nZ$$

are 3-aminopropyltrimethoxysilane, 3-aminopropyltriethoxysilane, 2-aminoethyltrimethoxysilane, 2-aminoethyltriethoxysilane, and 3-aminopropyltrichlorosilane. Other preferred examples of the compounds are N,N-diethylaminopropyltrimethoxysilane, morpholinopropyltriethoxysilane, trimethoxysilyl-3-propyl-N,N,N-dimethyloctylammonium chloride and trimethoxysilyl-3-propyl-N,N,N-dimethyloctadecylammonium chloride.

Preferably from 5 to 30 percent by weight, and more preferably from 10 to 20 percent by weight, of compounds of the formula

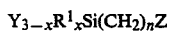
$$Y_{3-x}R^1{}_xSi(CH_2)_nZ$$

in which $R^1$, Y, Z, n and x are the same as above, are used, based on the weight of the untreated carrier.

In the dried hydrolysis products of functional silanes, the covalent bonds between the $NR_3$ groups or $-X^+NR_4$ groups and the carrier are formed during the preparation of the hydrolysis products, which can be produced by known methods, such as described by K. G. Allum et al., J. Organomet. Chem. 87, 203 (1975). The hydrolysis products may be modified by carrying out the hydrolysis in the presence of additional compounds such as waterglass, titanium halides or titanium alkoxides, zirconium halides or zirconium alkoxides, aluminum halides or aluminum alkoxides, silicon halides or silicon alkoxides, and tin halides or tin alkoxides.

Suitable examples of these compounds are $Si(OC_2H_5)_4$ and $(C_2H_5O)_3SiCH_2CH_2CH_2N(C_2H_5)_2$; $Ti(OC_4H_9)_4$ and $(CH_3O)_3SiCH_2CH_2CH_2N(CH_3)_2C_{18}H_{37}{}^{\oplus}Cl^{\ominus}$; $Na_2SiO_3$ and $(CH_3O)_3SiCH_2CH_2CH_2N(CH_3)_2C_{10}H_{21}{}^{\oplus}Cl^{\ominus}$; $Al(C_3H_7)_3$ and $(CH_3O)_3SiCH_2CH_2CH_2N(CH_3)_3{}^{\oplus}Cl^{\ominus}$.

Polystyrenes such as, for example, polystyrene crosslinked with divinylbenzene and having covalently bonded $NR_3$ groups or $-X^+NR_4$ groups are known and commercially available as basic ion exchange resins. Examples of preferred basic ion exchange resins are Amberlite IRA 93, and Amberlyst A21 (both available from Röhm und Haas GmbH, Frankfurt FRG), Lewatit 35A, Lewatit MP64, Lewatit MP65, and Lewatit MP62 (all available from Bayer AG, Leverkusen, FRG).

Preferably, the carriers with covalently bonded $NR_3$ groups or $-X^+NR_4$ groups are present as powders having an average particle size of from 1 $\mu$m to 1 mm or have been converted to shaped bodies, such as rings, half rings, rods, spheres or saddles in a manner known, per se, either before or after the $NR_3$ groups or $-X^+NR_4$ groups have become covalently bonded to the carrier.

The process of this invention is carried out in a heterogeneous phase, in which dichloromethylsilane is heated in a liquid or dissolved form in the presence of a solid catalyst in a suspension consisting of a finely divided catalyst having an average particle size of preferably from 10 $\mu$m to 1 mm, and more preferably from 1 $\mu$m to 1 mm, if desired, in the presence of an inert solvent, such as, for example, toluene, xylene, mesitylene, chlorobenzene, chlorotoluene, chloronaphthalene, dichlorobenzene, tetrachloroethane or tetrabromoethane, at a pressure of preferably from 2 to 20 bar at temperatures of preferably from 50° to 200° C., and the resultant low-boiling chloromethylsilane is separated off by means of a fractionating column. To prepare methylsilane, the chloromethylsilane obtained is heated together with the finely divided catalyst having an average particle size of preferably from 10 $\mu$m to 1 mm, and more preferably from 1 $\mu$m to 1 mm, and if desired, in the presence of an inert solvent, such as, for example, toluene, xylene, mesitylene, chlorobenzene, chlorotoluene, chloronaphthalene, dichlorobenzene, tetrachloroethane or tetrabromoethane, at a pressure of preferably from 10 to 100 bar at temperatures of preferably from 50° to 150° C. The resultant methylsilane is separated off by means of a fractionation column.

In the heterogeneous phase, the starting material is contacted in the gas phase with a solid catalyst which is present either in a finely divided form having an average particle size distribution of preferably from 10 $\mu$m to 1 mm, and more preferably from 0.1 mm to 0.5 mm, in a fixed or fluidized bed, or as a shaped body, in a fractionating column.

Preferred shaped bodies are in the shape of rings, spheres or cubes.

In the fixed or fluidized bed, dichloromethylsilane vapor is passed through a fixed or fluidized bed of finely divided catalyst at a pressure of preferably 0.1 to 100 bar and at temperatures of preferably from 50° to 400° C., and the resultant reaction mixture is condensed, and the chloromethylsilane is separated off by fractional distillation. Methylsilane is prepared by passing the chloromethylsilane in vapor form through a fixed or fluidized bed of finely divided catalyst at a pressure of preferably from 0.1 to 100 bar and at temperatures of preferably from 50° to 400° C. The resultant reaction mixture is condensed, and methylsilane is separated off by fractional distillation.

When the catalyst is present as a shaped body in a fractionating column, dichloromethylsilane is passed through the fractionating column at a pressure of preferably from 5 to 100 bar and at a temperature of preferably from 25° to 250° C. Depending on the dimensions of the column and the choice of the pressure and temperature conditions, chloromethylsilane, methylsilane or a mixture of chloromethylsilane and methylsilane is obtained at the top of column.

The shaped bodies are molded from finely divided catalysts having an average particle size distribution of from 1 $\mu$m to 1 mm, and if desired, with the addition of organic or inorganic binders or by means of crosslinking hydrolysis. The shapes can be formed by pressing at elevated temperature or by sintering at elevated pressure, but also by means of an extruder followed by comminution of the profiles.

Examples of organic or inorganic binders are epoxy resins, waterglass and organic polymers, such as polyethylene, polypropylene, polystyrene, polyvinyl chloride, polyacrylate and polyamide.

To increase the porosity of the shaped catalysts, a water-soluble substance such as sodium chloride or sodium sulfate is preferably added to the materials before shaping; and after the shaping step, the substance is then dissolved out, resulting in a highly active macroporous catalyst.

Chloromethylsilane and methylsilane are, for example, used in the preparation of organopolysiloxanes or in the preparation of tetralkylsilanes which are used as hydraulic oils in, for example, space technology.

EXAMPLE 1

A distillation apparatus made of V4A steel and consisting of a 3 liter capacity distilling flask with a flanged-on heating mantle and a magnetic stirrer, an inside thermometer and also one joint each for addition and removal of liquids, and equipped with a packed column, 1.5 m in length and 4 cm in inside diameter, filled with Raschig rings (6 mm in outer diameter, 6 mm in length), a mounted reflux condenser, a column head, a pressure-maintaining valve, a product cooler and a pressure-resistant receiver, was flushed with argon and then filled with 1726.5 g (15 mol) of dichloromethylsilane. After adding 172.65 g of dried ion exchange resin (available as Amberlite IRA 93 from Röhm & Haas, Frankfurt, FRG), the mixture was heated to 75° C. at a pressure of 2.5 bar. After a constant temperature of 32° C. has been reached at the column head, a continuous product flow of 250 g/h was removed at a reflux ratio of 10:1, while at the same time 800 g/h of dichloromethylsilane were pumped into the reactor via a metering pump. At the same time, the amount of the chlorosilane mixture necessary to keep the level constant was removed from the reactor, fractionally distilled at atmospheric pressure in a separate glass distillation apparatus consisting of a 2 liter flask with an ascending column, an inside thermometer and a mounted, mirror-coate, 3-part packed column having a lateral joint, a column head and a reflux condenser, the low-boiling components, consisting of dichloromethylsilane, which contained 10 percent by weight of chloromethylsilane, was returned to the storage container for addition to the pressurized reaction vessel. About 530 g/h of methyltrichlorosilane were obtained as bottom product.

Another experimental apparatus designed for higher pressures, which corresponds in its arrangement to the previous apparatus, but whose dimensions are smaller by a factor of 2, was charged with 800 g (10 mol) of chloromethylsilane together with 80 g of dried ion exchanger resin (available as Amberlite IRA 93 from Röhm & Haas, Frankfurt, FRG) under a pressure of 16 bar. As soon as a constant temperature of 30° C. has been reached at the column head, the addition of 250 g/h of chloromethylsilane was initiated. The low-boiling methylsilane was removed at the column head at a rate of 68 g/h (97 percent). The high-boiling dichloromethylsilane was concentrated in the bottom product. To maintain a constant liquid level in the distillation flask, a product flow was separated off continuously and added into the first pressurized distillation apparatus, where the mixture consisting of chlorcmethylsilane and dichloromethylsilane was reacted further with freshly added dichloromethylsilane.

EXAMPLE 2

A metering pump was used to introduce a volume flow of 125 g/h of dichloromethylsilane into an evaporator at a pressure of 1 bar. The resultant vapor was transferred to the base of a reaction tube, 50 cm in length and 2.5 cm in diameter, which had been heated to 100° C. and which contained 95.2 g of dried ion exchange resin (available as Lewatit MP 35 A from Bayer AG, Leverkusen, FRG). The escaping gas mixture was condensed, and some of it was reacted with 1-octene for analytical purposes.

Product composition:
  87.24 percent of dichlorcmethyloctylsilane
  12.36 percent of dioctylmethylchlorosilane
  0.39 percent of methyltrioctylsilane The condensed gas mixture was fractionally distilled to yield a mixture containing 97 percent chloromethylsilane and 3 percent methylsilane.

In a second stage, the resultant mixture was evaporated at a rate of 80 g/h and introduced into another reaction tube which had been heated to 100° C. and had the same dimensions as above and which contained 92.8 g of ion exchange resin (available as MP 64 from Bayer AG, Leverkusen, FRG). After reacting with 1-octene for analytical purposes the reaction product obtained had the following composition:
  77.38 percent of dioctylmethylchlorosilane
  13.57 percent of methyltrioctylsilane
  9.01 percent of methyloctychldichorosilane

EXAMPLE 3

Preparation of the catalyst

Method (A)

Ground and dried ion exchange resin (available as Lewatit MP 35 A from Bayer AG, Leverkusen, FRG) was coated onto Raschig rings made of glass, 6 mm in outer diameter and 6 mm in length, by means of an epoxy resin by introducing these rings into a solution of the epoxy resin which had already been mixed with a hardening agent and the solvent evaporated off. The sticky Raschig rings were added to a large excess of finely divided ion exchange resin, the mixture was poured back and forth a few times, and excess ion exchange resin was removed after a 24-hour hardening process.

Method (B)

Finely divided silica in the form of spheres having a diameter of from 4 to 6 mm (available as KC-Siliperl AF 125 from Kali-Chemie, Hannover, FRG), was heated for several hours with a solution of N,N-diethylaminopropyltrimethoxysilane in water-moist toluene. The mixture was filtered to remove the toluene, and the functional carrier was dried in vacuo at 100° C.

Disproportionation of dichloromethylsilane

About 800 g/h of dichloromethylsilane which had been continuously evaporated in an evaporator at a pressure of 20 bar was introduced from a storage vessel by means of a metering pump, into an apparatus made of V4A steel and consisting in its essential parts of an adjustable metering pump, an evaporator, a three-part packed column having a total length of 2.5 m and an inner diameter of 50 mm, a column head with a condenser, a 5 liter capacity distillation flask, and the necessary equipment for collecting the product and for removing the bottom product. The gas mixture was introduced into the lower part of the column filled with Raschig Rings 6 mm in outer diameter and 6 mm in length, and from there it entered the second part of the column packed with the functional catalyst prepared by method (B) above, with the resultant reaction mixture being separated at the same time. The higher-boiling methyltrichlorosilane flowed down and was collected in pressurized vessel from which it was released at a rate of 690 g/h via a metering pump and evaporated in an intermediate tank and transferred into a storage container. The low-boiling components flowed up into the third part of the column packed with the catalyst prepared by method (A) above. The vapor mixture formed was condensed at the column head by means of a condenser and the condensate removed from the distillation apparatus by means of an intermediate vessel. After further cooling, the product was transferred to pressure vessels. About 105 g/h of a silane mixture consisting of 94 percent of methylsilane, 5 percent of chloromethylsilane and 1 percent of dichloromethylsilane were obtained.

What is claimed is:

1. A process for preparing disproportionation products of dichloromethylsilane in the presence of a catalyst, which comprises contacting dichloromethylsilane with a catalyst consisting of a carrier which is insoluble in the reaction medium and which has $NR_3$ groups or $-X+NR_4$ groups covalently bonded thereto, in which R is selected from the group consisting of alkyl, aryl, or alicyclic groups which may contain heteroatoms as constituents of the ring, and hydrogen, and $X^-$ is selected from the group consisting of chloride, bromide and iodide.

2. The process of claim 1, wherein the alicyclic group contains a heteroatom as a constituent of the ring.

3. The process of claim 1, wherein the alicyclic group is free of a heteroatom as a constituent of the ring.

* * * * *